United States Patent
Loi et al.

(10) Patent No.: US 7,064,245 B1
(45) Date of Patent: Jun. 20, 2006

(54) PROCESS FOR RECONSTRUCTING A NON-HUMAN MAMMALIAN EMBRYO BY NUCLEAR TRANSFER USING A HEAT TREATED DONOR NUCLEUS AND PREPARAING A NON-HUMAN MAMMAL

(75) Inventors: Pasqualino Loi, Sassari (IT); Pietro Cappai, Sassari (IT)

(73) Assignee: Istituto Zootecnico E Caseario per La Sardegna, Sasari (IT)

( * ) Notice: Subject to any disclaimer, the term of this patent is extended or adjusted under 35 U.S.C. 154(b) by 0 days.

(21) Appl. No.: 09/980,557

(22) PCT Filed: Jun. 4, 1999

(86) PCT No.: PCT/IT99/00160

§ 371 (c)(1),
(2), (4) Date: Dec. 4, 2001

(87) PCT Pub. No.: WO00/74477

PCT Pub. Date: Dec. 14, 2000

(51) Int. Cl.
*C12N 15/00* (2006.01)

(52) U.S. Cl. ......................................... 800/24; 800/24
(58) Field of Classification Search ............... 800/8, 800/13–18, 24; 435/455, 463, 3
See application file for complete search history.

(56) References Cited

OTHER PUBLICATIONS

Westhusin et al. Theriogenology, vol. 55, pp. 35-49, 2001.*
Dinnyés et al. Cl;oning & Stem Cells, 4 :81-92 (2002).*
Fehilly et al. Nature, vol. 307, Feb. 16, 1984.*
Blakely et al. The Science of Animal Husbandry, Prentice-Hall, Inc., 5th Edition, 1990, pp. 257-261.*
Gómez et al. Theriogenology, 49:1143-1154 (Apr. 15, 1998).*
Schnieke et al. Science, 278:2130-2133 (1997).*
Kappell et al. Current Opinion in Biotechnology 3:548-553 (1992).*
Mullins et al. Hypertension 22:630-633 (1993).*
Houdebine. J. Biotech. 34:269-287 (1994).*
Mullins et al. J. Clin. Invest. 98:S37-S40 (1996).*
Cameron. Molec. Biol. 7:253-265 (1997).*
Sigmund. Arterioscler. Throm. Vasc. Biol. 20:1425-1429 (2000).*
Niemann. Transg. Res. 7:73-75 (1998).*
Meirelles et al. Complete Replacement of the Mitochondrial Genotype in a *Bos indicus* Calf Reconstructed by Nuclear Transfer to a *Bos taurus* Oocyte. Genetics 2001, vol. 158, pp. 351-356.*
Fehilly et al. Cytogenetic and Blood Group Studies of Sheep/Goat Chimaeras. J. Reproduct. Fertility. 1985, vol. 74, pp. 215-221.*
Pennisi et al. Clones: A Hard Act to Follow. Science. Jun. 9, 2000, vol. 288, pp. 1722-1727.*
A. Regelado and M. Song. Life Science: Cross-Species Cloning. The Wall Street Journal, Mar. 19, 2002.*
Korean Now, Oct. 7, 2000, Tiger Cloning on the Prowl.*
Galli et al. A Cloned Horse Born to Its Dam Twin. Nature. Aug. 7, 2003, vol. 424, pp. 635.*
Vanderwall et al. Cloned Horse Pregnancies Produced Using Adult Cumulus Cells. Reproduct. Fertil. Devel. 2004, vol. 16, pp. 675-679.*
Fitchev et al. Nuclear Transfer in the Rat: Potential Access to the Germline. Transplantation Proceed. 1999, vol. 31, pp. 1525-1530.*
Chense et al. Cloned Rabbits Produced by Nuclear Transfer from Adult Somatic Cells. Nature Biotechnology. Apr. 2002, vol. 20, pp. 366-369.*
Polejaeva et al. Cloned Pigs Produced by Nuclear Transfer from Adult Somatic Cells. Nature. Sep. 7, 2000, vol. 407, pp. 86-90.*

* cited by examiner

*Primary Examiner*—Deborah Crouch
(74) *Attorney, Agent, or Firm*—Browdy and Neimark, PLLC

(57) ABSTRACT

This invention relates to the generation of animals by the transfer of somatic cells which have been denatured preferably by heating, into enucleated metaphase II oocytes. This invention may be useful for the cloning of mammals including but not being limited to genetically selected and/or transgenic animals.

19 Claims, No Drawings

PROCESS FOR RECONSTRUCTING A NON-HUMAN MAMMALIAN EMBRYO BY NUCLEAR TRANSFER USING A HEAT TREATED DONOR NUCLEUS AND PREPARAING A NON-HUMAN MAMMAL

REFERENCE TO RELATED APPLICATIONS

The present application is the national stage under 35 U.S.C. 371 of international application PCT/IT99/00160, filed Jun. 4, 1999 which designated the United States, and which international application was published under PCT Article 21(2) in the English language.

FIELD OF THE INVENTION

The present invention relates to the field of the generation of animals, carried out by the reconstruction of the relevant animal embryos by nuclear transfer, including but being not limited to the generation of genetically selected and genetically modified animals.

BACKGROUND OF THE INVENTION

1. Introduction

Cloning by nuclear transfer is a classical example of how experimental models designed for basic research have been subsequently adopted by applied research.

In fact, the transfer of a differentiated cell into enucleated oocytes was suggested first by Spemann (Spemann H., Embryonic Development and Induction. Hafner Publishing Company, New York, 1938: 210–211) to see whether the totipotentiality of a nucleus from a differentiated cell became restricted during development. A large number of papers stemmed from that suggestion and culminated with the work of Briggs and King (Briggs and King, PNAS 1952, 38: 455–461) where nuclei taken from the intestinal epithelium transferred into enucleated Xenopus eggs developed into viable genetically identical animals, in the proper word, a clone.

Technical limitations restricted nuclear transfer to the Amphybia for 30 years before a seminal paper by McGrath and Solter (McGrath and Solter, Science 1983, 220: 1300–1302) initiated the modern development in mammalian cloning. This new era in nuclear transplantation was given further impetus by its use for cloning embryos from domestic species when nuclei of blastomeres taken from 16 cell stage sheep embryos were competent to support full development till normal lambs after transfer into enucleated oocytes (Willadsen S., Nature 1986, 320: 63–65). Since this article was published, many embryologists started to focus on nuclear transfer and several private companies set out for the commercial application of embryo cloning in the cattle industry.

2. Description of the Procedure for Nuclear Transfer

As a result of the efforts made in these years, the following procedure for reconstructing an animal embryo by nuclear transfer has been developed.

a. Individuation of a Recipient Cell

Metaphase II oocytes are commonly used as a recipient cytoplast for nuclear transfer, especially when the procedure is carried out on ungulates. However also fertilised one cell zygotes which had had both pronuclei removed can be used in principle as well.

When the former procedure is adopted, the oocytes, which can be maturated in vitro or in vivo and are usually collected after the appearance of the first polar body, are kept in hepes buffered medium containing Cytochalasin B, an inhibitor of microfilaments that confers the oolemma the plasticity necessary for the further manipulation exposed hereinafter.

b. Enucleation of the Recipient Cell

The oocytes so individuated are in fact usually enucleated prior to the transfer of the nucleus from the donor cell.

In the majority of economically important animals, the oocytes ovulates in the metaphase of the second meiotic division with the 2n chromatids arranged in a metaphase spindle underneath the first polar body. The high content of lipids renders the sheep cytoplasm quite dark thus making impossible, in contrast to other species like mouse and rabbit, the localisation of the chromosomes.

For that reason, the enucleation was originally carried out with a bevelled pipette by aspirating blindly a portion of cytoplasm underneath the first polar body. Because quite often the metaphase spindle migrates under the oocyte cortex, specially in aged oocytes, enucleation was successful only in 70–75% of the cases. The introduction of the vital dye Hoechst 33342, which binds reversibly to DNA (Tsunoda et al., J Reprod Fertil 1988, 82: 173–177) allows the precise localisation of the chromosomes after UV exposure and is widely used in nuclear transfer.

c. Identification of a Donor Cell

Fully or partially differentiated cell or also an undifferentiated cell can be used as a donor cell (the so called "karyoplast": blastomeres from an early embryo or somatic cells). Such a donor cell can be both cultivated in vitro and abstracted ex vivo, provided that it has however a normal content of DNA and is karyotipically normal. More preferably are used cells in G0 or G1 phase as in fact, it is the only cell cycle stage that guarantees a correct ploidy after embryo reconstruction (Campbell et al., Rev of Reprod 1996, 1: 40–46). No development of embryo has ever been obtained using as a donor cell non-living cells.

d. Possible Genetic Modification of the Chromatin of the Donor Cell

The nucleus of the donor cell can be genetically modified prior to the transfer in the recipient cell, in order to obtain transgenic animals. The term "transgenic" cover not only the animal containing at least one gene from another species in their somatic and germ line, but any animal whose germ line is subjected to technical intervention by recombinant DNA technology.

e. Nucleus Transfer from the Donor Cell to the Recipient Cell

The nucleus of such a donor cell is therefore transferred in the recipient cell. Such a transfer can be carried out by two different procedures: i) cell fusion and ii) nuclear injection. According to the former procedure, which is the most commonly adopted for nuclei of big dimension, the donor cell as a whole is then inserted by the same enucleation pipette used for the enucleation of the recipient cell in the relevant perivitelline space. The reconstructed embryo is then placed in a fusion chamber between two platinum wires whose gap is filled with fusion medium (0.3 M mannitol with 0.050 mM $CaCl_2$ and 0.100 mM $MgSO_4$). Cell fusion is induced by one or more electrical pulses of direct current applied perpendicularly to the two fusion partners. The frequency of fusion is proportionally related to the area of contact between cytoplast and karyoplast and it is usually high in the case of blastomeres, but it becomes sensibly lower in the case of small foetal or somatic cells. The electric pulse opens temporary pores in the adjacent membranes and the cytoplasmic communication established between karyoplast and cytoplast starts the fusion process which is usually completed within one hour; meanwhile, an influx of extracellular calcium ions induces the activation of the oocyte (Sun et al., Development 1991, 115: 947–956).

According to the procedure reported on point ii) above, the nuclear transfer is carried out by microinjection of the donor nuclei with a process which is getting more used when small cells have to be transferred. The final outline of the process is however the same as the transfer carried out by cell fusion with minimal modification (Collas P and Barnes F L., Mol Reprod Dev 1994, 38: 264–267; Wakayama et al., Nature 1998, 394: 374).

f. Transfer of the Embryo in a Recipient Animal

The successfully fused couplets or microinjected oocytes are embedded in agar chips and transferred into the oviduct of a temporary recipient animal. The embedding is a necessary procedure that protects the embryos from immunocompetent cells present in the oviductal lumen.

After seven days the oviducts are flushed back and those embryos that developed to blastocysts or morulae are dissected out from the agar and transferred to synchronous recipients for development to term.

3. Technical Problem

Despite the efforts done by many laboratories, the efficiency of cloning in terms of offspring production has been invariably low and unpredictable (Bondioli et al., Theriogenology 1994, 33: 165–174) for several years.

This low efficiency was primarily due to the empirical approach used for nuclear transfer.

As a consequence of the studies made in the last years some of the technical limitations, which such a low efficiency was due to, were evidenced.

In particular basic studies undertaken in the last five years on the understanding of nuclear cytoplasmatic interaction in reconstructed embryos clarified how at least one of the reasons for the poor development of cloned embryos is the cell-cycle combination, indicating also the ideal combination for reconstructing embryos by nuclear transfer (Collas et al., Biol Reprod 1992, 46:492–500; Barnes et al., Mol Reprod Dev 1993, 36: 33–41; Campbell et al., Biol Reprod 1994, 50: 1385–1393; reviewed by Campbell et al., Rev of Reprod 1996, 1: 40–46).

Another, insurmountable, limit of embryo cloning was identified in the limited number of nuclei obtainable from an individual embryo. In this connection however the ability to use cultured cell lines derived from embryos have offered a large number of advantages over the use of cleavage stage embryos.

In this connection the ideal cells for this purpose were firstly identified in the embryonic stem cell (ES), which however, unfortunately, have not been isolated from embryos of large animals (Galli et al., Zygote 1994, 2: 385–389).

The production of the first sheep cloned from cultured cell line derived from embryos overcame this limit (Campbell et al., Nature 1996, 380: 64–66) opening new and important opportunities in both basic and applied research. The possibility to use cultured cells not only represented the ideal solution to the production of a large number of high genetic merit or genetically modified animals, but also the distinct cell cycle phases displayed by cells in culture opens the possibility to work out the ideal cell-cycle combination for nuclear transfer of differentiated cells.

This seminal paper was in fact immediately followed by other two, the report of the first mammal produced by the nuclear transfer of a somatic cell (Wilmut et al., Nature 1997, 385: 810–813) and the first transgenic lambs produced by nuclear transfer of genetically modified cells (Schieke et al., Science 1997, 278: 2130–2133).

After that two subsequent reports referring to somatic cloning in mice and cow respectively confirmed the fact that the animal resulting from such a process is effectively a clone (Wakayama et al., Nature 1998, 394: 369–374; Kato et al., Science 1998, 282: 2095–2099).

Further progress made in the last years made embryo cloning a reliable technology potentially applicable in animal breeding (Heyman Y and Renard JP, Anim Reprod Science 1996, 42: 427–436; Loi et al., Theriogenology 1997, 48: 1–10; Loi et al., Biol of Reprod 1998, 58: 1177–1187).

Reprogramming of the Nucleus of the Donor Cell

From all these reports it can be concluded that at least a small proportion of somatic nuclei can be developed into viable offspring, and that such a development is strictly consequent to the success in the "reprogramming" of the donor nucleus which occur in the oocyte immediately after transfer. What it is still not clear is the mechanism that regulates this reprogramming which is in fact due to unknown factors present in the cytoplast.

Following transplantation into oocytes, somatic nuclei lose in fact part (or all in the case of Dolly: see Campbell et al., Nature 1996, 380: 64–66) the structural components of the chromosomes that maintain their differentiated state and gain the capacity to execute the regulated expression of genes through embryonic and fetal development (Patterton and Wolffe, Dev Biol 1996, 173: 2–13).

Basically, the differentiation process which starts concomitantly with the activation of the embryonic genome (it does occur in sheep at the 5th cell cycle, 8–16 cell transition) is completely reversed after nuclear transfer, and the transferred nucleus behaves like a zygote.

Somatic nuclei transplanted into mature eggs are therefore remodelled and this morphological change is associated with the re-acquisition of pluripotency, and in some cases, totipotency (Gurdon I., J Embryol Exp Morphol 1962, 10: 622–640).

The molecular machinery responsible of such a remodelling (and therefore reprogramming) of the genome (diploid, somatic or whatever genome) transferred into the oocyte is not yet fully clarified. However as of course no specific and efficient molecular mechanism for this purpose could have been developed in the oocyte during the evolution for a differentiated cell nucleus inserted in the oocyte itself, such a mechanism is deemed to be the same which operates on the aploid spermatozoo genome at the time of activation.

Following fertilisation, the sperm nucleus is in fact rapidly remodelled by the egg cytoplasm to assemble the paternal pronucleus. The assembly of the pronucleus requires the molecular chaperone nucleoplasmin (Philpott et al., Cell 1991, 65: 569–578). Nucleoplasmin specifically removes the basic, sperm specific proteins and on the same time deposits histones H2A.X and H2.B onto chromatin (Philpott and Leno, Cell 1992, 69: 759–767). The resulting specialised chromosomal conformation found in the pronucleus is also maintained in nuclei of cleavage stage embryos (Dimitrov et al., J Cell Biol 1994, 126: 591–601).

Similarly, there is experimental evidence that nucleoplasmin plays also a major role in the remodelling of somatic nuclei strictly linked to the acquisition of totipotency of somatic nuclei, which requires the release of chromatin components and the uptake of structural and regulatory proteins from the cytoplasm (Philpott et al., Cell 1991 65: 569–578; Wangh et al., J Cell Science 1995, 108: 2187–2196).

In particular it has been observed that the specific dissociation of somatic linker histones H1 and H1° associated with the incorporation of oocyte-specific linker histone B4 into the remodelled chromatin mediated by nucleoplasmin, increases the trascriptional competence, and thus the totipotence of somatic nuclei (Dimitrov and Wolffe, the EMBO Journal 1996, 15: 5897–5906).

While however the nucleosomal transition during remodelling have been described in detail (for review see Patterton and Wolffe, Dev Biol 1996, 173: 2–13), the regulation of long-range chromatin structure during development is far less clear. There is increasing evidence that high order chromatin structures play a role in the acquisition and maintenance of the committed status of the cells. In particular, it has been shown that the protein of the SMC (Segregation of Mitotic Chromosome) and chromodomain families are important for transcriptional control (Chang et al., Cell 1994, 79: 459–474; for review see: Patterton and Wolffe, Dev Biol 1996, 173: 2–13).

From the above consideration it was suggested that changes in the chromatin structures can facilitate the reprogramming of the transferred nucleus upon the relevant transfer (Wilmuth I. et al., Nature 1997, vol. 385, pag. 810–813; Campbell et al., 1996), and that more accessible is the chromatin to cytoplasmatic remodelling factors, better chances the nucleus has to be completely reprogrammed upon nuclear transfer.

In particular it was suggested that the reduced transcriptional activity of quiescent cells may be beneficial for reprogramming (Campbell et al., 1996), although no direct comparison has been done with nuclei in different stage of the cell cycle.

Also, the displacement of sequence-specific transcription factors from mitotic chromatin (Martinez-Balbas et al., Cell 1995, 83: 229–238) positively influences the remodelling of mitotic cells into metaphase cytoplasm (Fulka et al., BioEssay 1996, 18: 835–840) and consequently induces a better reprogramming as indicated in mice experiment (Kwon and Kono PNAS 1996, 93: 13010–13013).

Such a displacement is a "physiological" consequence of the reduced metabolic activity in starved G0 cells (Campbell et al., Nature, 1996), and a consequence of a prolonged chromosome condensation in the method suggested by Wakayama (Wakayama et al., 1998). In both cases, the displacement or the termination of transcriptional activity falls into the normal activity of the cell and it is not "per se" responsible for genome reprogramming as clearly indicated by the fact that the phenotype of the cell is stably maintained after both cell cycle stages. However, despite the use of a highly defined synchronous population of G0 nuclei donors, or the uniform, prolonged exposure of the transferred nuclei into the cytoplasmic environment, less than 2% of nuclei are fully reprogrammed and develop into viable young upon nuclear transfer. Considering that the oocyte cytoplasm would normally encounter a transcriptionally inactive sperm nucleus rather than a fully differentiated nucleus, the low efficiency resulting from the above procedures is unsurprising. No alternative procedures have been suggested so far and foremost more invasive procedures that may lead to the loss of cell viability for two reasons: firstly, nuclear transfer is still accomplished by electro-mediated cell transfer, this method working only with living cells, secondly, a no-living cell is commonly believed to not be a good candidate for nuclear transfer.

In spite of the fact that numerous studies have indicated that high temperatures denature proteins and nucleic acids with a melting transition occurring when the temperature exceeds 55° C. (Pain RH., Symp Soc Exp Biol 1987, 41: 21–33), and that the denatured state of proteins is the primary target for degradative enzymes (McLendon and Radany, J Biol Chem 1978, 253: 6335–6337)— and therefore in the specific case also for the specific proteasome activity present in mature oocytes (Saro CK and Hoschi M, J Biochem 1997, 122: 286–293)— the elimination of such factors by the denaturation and subsequent degradation by degradative enzymes, was not considered in art.

In this connection, however it shall be kept into account the proved existence of a real epigenetic "cell memory" which is necessary for maintaining a stable pattern of gene expression in dividing cells, and allows the cellular phenotypes of differentiated cells to be stably propagated through cell division.

DNA methylation and the propagation of specific chromatin structures are in particular suggested as good candidates for the maintenance of the cell memory (Patterson and Wolffe, Dev. Biol 1996, 173: 2–13). Alternatively or concomitantly, some factors might remain bound to mitotic chromosomes acting as bookmark for those genes that must be re-expressed.

The same consideration can be drawn for quiescent G0 cells. These cells are still metabolically active, although at reduced levels, and no longer proliferated unless called to do so by appropriated extracellular signals. Of course, the phenotype of quiescent cells does not change after re-activation indicating that a stable pattern of gene expression is maintained by specific chromatin structures during G0 too.

Accordingly both mitotic and quiescent cells retain the epigenetic cell memory that maintains the differentiated status. The essential condition for a full reprogramming of a somatic cell is therefore its complete remodelling which involves a transition in chromosomal structures and composition associated with the acquisition to carry out the rapid cleavage cycle of early development and to execute the regulated expression of genes through embryonic and fetal development till the birth of a normal, viable animal.

Two distinct approach have been suggested for the induction of full reprogramming of somatic nuclei. The first, postulated by Campbell and co-workers (Campbell et al., Nature 1996, 380: 64–66) says that nuclear quiescence inducted by serum deprivation is the fundamental condition for nuclear reprogramming; the second one, claimed by Wakayama (Wakayama et al., Nature 1998, 394: 369–374), but also anticipated by Campbell (Campbell et al., Nature 1996, 380: 64–66), says that a prolonged exposition of the nuclei into the cytoplasm environment increases the chances for nuclear reprogramming.

However, the importance of nuclear quiescence for somatic nuclear transfer is still controversial. In fact, in the first report on the use of G0 cells as nuclei donors (Campbell et al., Nature 1996, 380: 64–66) no comparison is done with cells in other stages of the cell cycle. The situation did not change in the following report (Wilmut et al., Nature 1997, 385: 810–813) where quiescent cells from three different cell lines, embryo, fetal and adult derived cells have been used as nuclei donors.

Moreover, actively proliferating fetal fibroblast cells have been shown to direct normal embryonic and fetal development in the cow (Cibelli et al., Science 1998. 280: 1256–1258) and no differences in blastocysts production were found between proliferating and quiescent somatic and fetal bovine cells in a recent comparative study (Le Bourhis D et al., Clevage et Insemination 1998, Octobre, n 287, 3–9).

So the question is: why, although nearly all the cells used for nuclei transfer are in G0, only a small proportion, 2%, develop into viable offspring? What helps those cell to gain a full totipotency after nuclear transfer?

SUMMARY OF THE INVENTION

It is an object of the present invention to provide a process comprising the denaturation of the nucleosomes and chromatin of the donor nuclei before nuclear transfer. This denaturation facilitates a more complete reprogramming of differentiated somatic, embryonic or fetal derived cells prior to nuclear transfer.

In particular such denaturation can be carried out by heat-treating of the chromatin of the donor cell, which results in the thermal denaturation of nucleosomes as well as long-range chromatin structures, and in favouring the complete remodelling of donor nuclei prior to nuclear transfer.

In particular the denaturation by thermal treatment affects the structural proteins involved in the maintenance of the differentiate state.

In the present study we estimated the efficiency of nuclear transfer using thermally destabilised donor cells from adult ewes. The rationale was that the heat treatment would produce chromatin more amenable for reprogramming as a result of the denaturation of DNA regulating proteins. Given that denatured proteins are more readily degraded by proteolytic enzymes (Parsell and Sauer, J. Biol. Chem. 1989, 264; 7590–7595), it was reasoned that the oocyte proteolytic machinery (Tokumoto T. International review of cytology, 1999, 186; 261–294) may more readily process nucleosomal and chromatin protein complexes following thermal denaturation. It was considered that the resulting DNA might then be more accessible to programming factors present in the ooplasm.

The scientific explanation of the success of the process according to the present invention, which however do not bind the relevant scope, is that while the oocyte owns the molecular machinery for remodelling somatic chromatin at nucleosomal level, the oocyte itself does not have the specific pathways for remodeling long-range chromatin structures present in G0 or condensed chromatin. Presumely, the full reprogramming of somatic nuclei is accidentally induced by non-specific remodelling activity of nucleoplasmin and/or alternatively, may be that the small proportion of successfully reprogrammed cells are degenerating or early apoptic cells, in other words, they may have lost a tight control of gene expression.

The present invention can be used for basic research and also applied to all mammalian species excluding human beings, in particular to economically important ungulates: cattle, sheep, goats, pigs, water buffalo, horses and also laboratory animals: mice, rabbits, guinea pigs or fur animals. The invention is applicable for the production of high genetic merit animals, endangered species and transgenic animals. It should be noted that for "transgenic" animal it is not intended only an animal carrying in his genome one or more genes from other species, but also animals whose genome has been modified somehow by recombinant DNA technology.

In the case the present method is applied for the production of a transgenic animal, the donor nucleus may be genetically modified to contain one or more transgenes before its use for nuclear transfer. The donor nuclei may be genetically modified by the different procedures now available: transfection, electroporation, viral transfection, lipofection and gold microprojectile bombardment.

There are several applications of the present invention both for basic and for applied research. The knowledge of the thermal stability of the different families of DNA regulatory proteins, associated with the method of nuclear transfer here proposed, may provide unique insights on the mechanism of genome reprogramming. For the first time, it has been proved that no-living cells can be efficiently reprogrammed upon transfer into enucleated oocytes. This fact certainly has several practical applications, one of which may be the possibility to create genetic banks at low cost for the preservation of rare and endangered species. Most of engendered species are living in Africa where environmental conditions render un-practical the use of liquid nitrogen (−196° C.) for cell storage as indicated by FAO experts in occasion of the workshop "The implication of development in biotechnology for the conservation of animal genetic resources at risk: reversible DNA quiescence and cloning". A report of the workshop is available at FAO homepage http://www.fao.org/. The fact that no-living cells can develop into embryos and fetus following nuclear transfer opens for the first time the possibility to store cells in cheaper systems like in a freeze-dried status. This would have a dramatic impact for the creation of genetic banks for endangered species. Being cell viability not longer the absolute requisite for cloning, it will be possible to increase dramatically the extent of genetic manipulation before nuclear transfer. It might be possible to produce an individual simply by assembly single chromosomes from different inter-intra-specific individual provided that a functional centriole is injected together with the chromosomes.

As a consequence of what set forth above and below the object of the present invention is a process for reconstructing an animal embryo, comprising the following operations:

identification of the chromatin which will constitute the chromatin of the animal embryo, said chromatin being selected from at least one donor cell;

denaturation of said chromatin;

transfer of the denaturated chromatin into a recipient cell.

The chromatin can be organized in chromosomes, which can be selected from more than one donor cell.

Specific embodiments are the cases wherein the donor cell is collected from a single individual or from different individuals, which can belong to a single species or to different species. The donor cell can be cultured or extracted ex vivo, preferably in G1 or G0 phase but also in M phase, provided that the ploidy is corrected after nuclear transfer; the donor cell can be further freeze-dried or dead, and can be in particular an embryonic cell, a foetal cell, a somatic cell or a granulosa cell.

In another embodiment of the invention the chromatin is subjected to at least a genetical modification, which can consist in the insertion of at least an etherologous DNA sequence, the deletion of at least one homologous gene, the modification of at least one homologous gene, and the duplication of at least one homologous gene.

The denaturation of the chromatin can in particular be carried out directly on the nucleo-protein assembly, on the nucleus inside or outside the donor cells, by selecting a combination of temperature, pH, ionic strenght and other chromatin-destabilizing agents, or by heat-treating. In the last case the temperature can be the melting temperature of the transcriptional regulatory proteins, and in particular a range from 45° C. to 95° C., wherein the preferred embodiments are 55° C. and 75° C.

The recipient cell is usually an oocyte, in metaphase II matured in vitro, which is enucleated prior to the transfer of the nucleus of the donor cell, and the nuclear transfer is preferably carried out by injection.

The resulting animal embryo belongs to a non-human mammalian species in particular can be a mouse, a rat, a rabbit, a guinea pig, a fur, or an ungulate species like cattle, sheep, goat, pig, water buffalo and horse.

A further object of the present invention is a process for preparing an animal, comprising the following operations:
a. reconstructing an animal embryo;
b. culture of the reconstructed embryo;
c. transfer of the blastocysts into a suitable recipient animal;
d. causing said animal embryo to develop to term, after transfer into a suitable recipient animal. Such a process can further comprise the operation of the breeding from the resulting animal.

In a particular embodiment, the embryo of the operation a. is subcloned for obtaining more than one animal developing to term, and is a genetically modified embryo resulting from the process described above. The embryo can be also genetically modified before the operation a. prior to the development to term, and the operation c. can be carried out in vitro or in vivo by transferring the embryo in a temporary recipient animal.

A further object of the present invention is the reconstructed animal embryo and animal, resulting from the processes described above. Such an animal can be transgenic or not, and in particular can be a laboratory animal or an ungulate, as described above.

DETAILED DESCRIPTION OF THE INVENTION

The process of the present invention involves the transfer into a suitable recipient cell of a diploid nucleus from a donor cell after being denatured by an appropriate combination of temperature, pH, ionic strength and other chromatin-destabilising agents. In particular the denaturation has been carried out by heating the cell in Hepes buffered medium at 55° C. or 75° C. The relevant treatment is exemplified in the Example 1.

Preferably a granulosa cell is used to this purpose, even if the process of the present invention is not restricted to granulosa cells only; all cells from an adult animal, including also embryonic and fetal cells, may be used given the fact that they are normal diploid G1 or G0 cells.

Cells may be or may be not cultured prior to nuclear transfer. However, culture is necessary when this invention is used for the generation of transgenic animals. In fact, the application of the molecular biology technologies for genetic modification of a cell population requires the culture of the cells either for the transformation and for screening and selection of the successfully modified cell clones.

After the treatment exemplified in Example 1 below, the nuclei are therefore transferred into enucleated metaphase II oocyte. The oocyte is enucleated by micromanipulation after the localisation under UV light of the chromosomes; however, the present method is not restricted to the above procedure but also alternative solutions like non-invasive approaches like UV irradiation for enucleation will be also considered.

The recipient oocytes may be produced by superovulation of donor ewes or more conveniently in vitro from ovaries collected at the abattoir according to the protocol given in the following Example 2 in vitro maturation of sheep oocytes. In vitro maturation of oocytes collected by individual females of high genetic merit or transgenic will be necessary in the case the invention is applied to the multiplication of the oocyte donors themselves, or alternatively, when a particular cytoplasmatic background is required.

Since the method herein proposed involves the denaturation of the cells by heating or other suitable denaturating agents, electro-mediated cell fusion cannot be used for nuclear transfer, therefore the injection of the treated nuclei will be the preferred method.

The injected cytoplasts is activated with one of these methods: one or more electrical pulses, ionomycin-6DMAP association (Loi et al., Biol Reprod 1998, 58: 1177–1187), or ionomycin plus cycloheximide (Presicce and Yang, Mol Reprod Dev 1994, 37: 61–68). Following activation, the reconstructed embryos can be embedded in agar (Willadsen S., Nature 1979, 277: 298–300) and cultured in vivo into ligated oviduct of temporary recipient ewes according to the method previously published (Loi et al., Theriogenology 1997, 48: 1–10) or more conveniently cultured in vitro according to the method described in Example 2. Culture in vitro will be also preferred in the case the cloned embryos must be used themselves as nuclei donors for a serial nuclear transfer in order to further amplify the number of valuable cloned animals. After a suitable period of culture in vitro, usually 6–9 days, the embryos which develop to blastocyst stage are transferred into recipient ewes for development to term. Cloned animals generated with the present method may be breed and used for creating a flock of animals with the predicted characteristics.

The process of the present invention for the reconstruction of an animal embryo in its preferred embodiments comprises eventually the following steps:
1) selection of a suitable donor cell which can be directly taken from the desired animal or from cultured cell lines in the case a genetically modified cell is used for the production of a transgenic animal
2) heat treatment of the cells to be used as nuclear donor
3) embryo reconstruction by injection of heat-treated cells
4) culture in vitro or in vivo of the reconstructed embryo
5) transfer of the blastocysts into final recipients.

Thermal destabilised nuclei developed in higher proportion to blastocysts in comparison to control embryos reconstructed with fresh, untreated cells (see Table 1 with the results of Example 2).

In the accompanying Example 1, the cells are heated in Hepes buffered Synthetic Oviductal Fluid (SOF) but whatever medium, whose ionic strength and pH have optimised for chromosome destabilisation, may be preferred. Two temperatures have been selected in the present application, 55° C. and 75° C., but intermediate or higher temperatures may exert a better effect onto genomic reprogramming.

In case of the generation of a transgenic embryo after the operation 1) and before the operation 2) the two following additional operations shall be carried out:
1a) genetic modification of the cultured cells with the more suitable DNA recombinant technology; this may include: gene knock-out, deletion, addition, duplication and other gene modifications;
1b) screening and selection of successfully modified cells.

So far a general description has been given of the present invention. With the aid of the following examples, a more detailed description of specific embodiments will now be given, in order to give a better understanding of the objects, characteristics, advantages and operating methods of the invention. Such examples serve merely to illustrate and do not limit the scope of the present invention, which is defined in the annexed claims.

EXAMPLES

Example 1

Heat-Denaturation of the Donor Cell

Pooled granulosa cells from Cumulus Oocyte Complexes (COCs) have been used throughout the examples although other kind of cells may be used. COCs were incubated in hyaluronidase (300 UI/ml) for few seconds then dissociated into a single cell population by vigorous pipetting. Cells were washed twice in Hepes SOF and heated in Hepes SOF at either 55° C. and 75° C. in a water bath for 15 minutes. After the treatment, the cells are centrifuged, re-suspended in manipulation medium (Hepes buffered TCM 199+4 mg/ml BSA) and used for nuclear transfer within one-two hours.

Freeze-Drying of Granulosa Cells

An aliquot of granulosa cells taken from in vitro matured oocytes was centrifuged and the resulting pellet re-suspended with 100 µl of Hepes TCM 199 plus 7% DMSO (Dimethylsulphoxide), loaded into 2 ml glass ampoules and directly plunged in liquid nitrogen (−196° C.). Frozen cells were placed in a pre-cooled aluminium block and freeze-dried in a lyophilizer (Edwards). Freeze-dried cells were kept in the dark at room temperature until use.

Before the use for nuclear transfer the freeze-dried cells were re-hydrated with 100 µl of Milli-Q water and heat treated as described in Example 1.

Example 2

Embryo Reconstruction by Nuclear Transfer Oocyte in Vitro Maturation

Ovaries were collected immediately after slaughter and transported to the laboratory in saline at approximately 35° C. within 1–2 hours. Oocytes were obtained by dissection of ovaries in TCM-199 enriched with 5% calf serum, 0.05 mg/ml heparin, 0.05 mg/ml gentamicin sulphate.

Follicular oocytes were evaluated under the stereomicroscope and only these covered by at least 2 layers of granulosa cells and with evenly granulated cytoplasm were selected for IVM. The medium used for maturation was bicarbonate-buffered TCM-199 with the osmolarity adjusted to 275 mOsm/Kg and glutamine present at the concentration of 2 mM. Maturation medium was enriched with 10% fetal bovine serum, 5 µg/ml FSH (Ovagen, ICP, New Zealand) 5 µg/ml LH, 1 µg/ml estradiol, 0.3 mM sodium piruvate and 100 µM cysteamine. Oocytes were incubated in 0.4 ml of medium in 4-well dishes (Nunc, Nunclon, Denmark) covered with mineral oil. IVM conditions were 5% $CO_2$ in a humidified air at 39° C. for 24 hours.

Embryo Reconstruction

Metaphase II oocytes were stripped off from the cumulus cells and incubated for 15 minutes in the presence of 51 g/ml Hoecsht 33342. Enucleation was accomplished in manipulating medium (Hepes TCM 199+4 mg/ml BSA) supplemented with 7.5 µg/ml Cytochalasin B. The oocytes were immobilised with a holding pipette and exposed for 2–3 seconds to UV light for the localisation of the chromosomes. A portion of cytoplasm with the metaphase spindle was then aspirated into the enucleation pipette. Enucleated oocytes were put back in culture for 30 minutes in order to wash off the Cytochalasin B.

The same medium was used for nuclear transfer. Fresh cells were picked up and down with a injection pipette (4 µs) until the membrane was completely destroyed, then the nucleus injected into the oocyte. Heat-treated cells were injected with a broader pipette (10 µs) with the same procedure.

Oocyte Activation

Immediately after injection, the reconstructed embryos were activated with 5 minutes treatment of 5 µM ionomycin followed by 5 hours incubation at 38.5° C. in SOF supplemented with 10 µM cycloeximide. After 5 hours, the reconstructed embryos were cultured in vitro for 7–9 days.

In Vitro Culture

The reconstructed embryos were allocated to 20 µl culture drops consisting of SOF supplemented with 2% (v/v) BME-essential amino acids, 1% (v/v) MEM-nonessential amino acids, 1 mM glutamine and 8 mg/ml BSA-fatty acid free. At 3rd and 5th day of culture (day O— the day of nuclear transfer) 5% charcoal stripped FBS was added to the medium. Culture was continued until 9 days, then reconstructed embryos that developed to blastocyst stage were transferred to synchronised recipients.

Results of Example 1

The heat treatment killed all the cells and induced an evident denaturation in all the cell compartments including the cytoplasmatic membrane which was completely removed.

Heated freeze-dried cells displayed the same features than the fresh ones.

The results of Example 2 are Summarised in Table 1.

TABLE 1

Development to blastocyst stage of fresh and heat-treated granulosa cells transplanted into enucleated metaphase II oocytes.

| treatment | n injected | cultured | blastocysts (%) of embryo cultured |
|---|---|---|---|
| fresh | 230 | 127 | 8 (6%) |
| 55° C. | 301 | 229 | 29 (12.6%) |
| 75° C. | 215 | 120 | 33 (27.1%) |

In average, 60% of cultured embryos in fresh group and more than 70% in both 55 and 75° C. groups developed to morula stage (range: 2–25 cells); however, only blastocysts stage embryos were considered.

Blastocysts from all groups (total n. 50) were transferred into recipient ewes for development to term, the results are summarised in Table 2.

TABLE 2

| group | | n | pregnancies detected by ultrasound scanning | | | |
|---|---|---|---|---|---|---|
| recipient | (° C.) | blastocyst | day 40 | day 60 | day 80 | offspring |
| 8013 | 55 | 3 + 1 morula | + | + | − | |
| 3961 | 55 | 3 | + | − | − | |
| 5836 | 55 | 2 | − | − | − | |
| 2239 | 55 | 3 | + | + | + | |
| 2554 | 55 | 2 | + | − | − | |
| 2582 | 55 | 2 | − | − | − | |
| 6509 | 55 | 2 | + | + | − | |
| 2640 | 55 | 2 + 1 morula | + | + | + | + |
| 5734 | 55 | 3 | + | − | − | |
| 9007 | 55 | 3 | + | + | − | |
| pregnancy rate | | | 80% | 30% | 20% | |
| 5651 | fresh | 1 | − | − | − | |
| 6801 | fresh | 2 | + | + | − | |
| 2727 | fresh | 2 | + | − | − | |
| 4893 | fresh | 3 | − | − | − | |
| pregnancy rate | | | 50% | − | | |

TABLE 2-continued

|  |  |  | pregnancies detected by ultrasound scanning | | | |
|---|---|---|---|---|---|---|
| recipient | group (° C.) | n blastocyst | day 40 | day 60 | day 80 | offspring |
| 8147 | 75 | 4 + 2 morule | + | | | |
| clone | 75 | 3 | + | | | |
| pregnancy rate | | | 100% | | | |

Three recipients are not examined yet so the proportion of pregnant animals is likely to change.

TABLE 3

Development of embryos reconstructed with denaturated, freeze-dried granulosa cells

| group | n. injected | n. cultured | embryos (morula stage) |
|---|---|---|---|
| freeze dried 75° | 72 | 47 | 28 (59.5%)* |

*no embryo developed to blastocyst in these preliminary trial probably because the quality of the oocytes used as a recipient cytoplast was very poor. However, it is not excluded that freeze-dried cell can be successful reprogrammed by the method proposed in the present invention.

What is claimed is:

1. A process for reconstructing an animal embryo of a species selected from the group consisting of mouse, cattle, sheep and goat, comprising:
    a. transferring into a recipient cell a diploid nucleus from a donor cell or the donor cell including said nucleus, said donor cell being a $G_1$ or $G_0$ cell from the same species and said recipient cell being an enucleated metaphase II oocyte of a non-primate mammalian species, wherein the chromatin within said nucleus is subjected to denaturing by heat-treating carried out at melting temperature of the transcriptional regulatory proteins before transferring the nucleus into the recipient cell; and
    b. further activating and culturing the recipient cell in vitro or in vivo.

2. The process according to claim 1, wherein said heat-treating is carried out at a temperature range of from 45° C. to 95° C.

3. The process according to claim 2 wherein said heat-treating is carried out at 55° C.

4. The process according to claim 2, wherein said heat-treating is carried out at 75° C.

5. The process according to claim 1, wherein said donor cell is selected from the group consisting of embryonic cells, fetal cells, and somatic cells.

6. The process according to claim 1, wherein said donor cell is a cultured cell.

7. The process according to claim 1, wherein said donor cell is a granulosa cell.

8. The process according to claim 1, wherein said donor cell is a non-living cell.

9. The process according to claim 1, wherein said chromatin is subjected to at least one genetic modification.

10. The process according to claim 9 wherein said genetic modification comprises the insertion of at least one heterologous DNA.

11. The process according to claim 9 wherein said genetic modification comprises the deletion of at least one homologous gene.

12. The process according to claim 9 wherein said genetic modification comprises the modification of at least one homologous gene.

13. The process according to claim 9 wherein said genetic modification comprises the duplication of at least one homologous gene.

14. The process according to claim 1, wherein said denaturing treatment is carried out on the nucleus, said nucleus being inside the donor cells.

15. The process according to claim 1, wherein said oocyte is matured in vitro.

16. The process according to claim 1, wherein the nuclear transfer is carried out by injecting the donor nucleus into the recipient cell.

17. A process for generating an animal selected from the group consisting of moue, cattle, sheep, and goat comprising:
    a. culturing an animal embryo reconstructed according to claim 1 to obtain blastocysts;
    b. transferring the blastocysts into a suitable recipient animal;
    c. causing said blastocysts to develop to term and further breeding the resulting animal.

18. The process according to claim 17, wherein the embryo of step a is a genetically modified embryo.

19. The process according to claim 17, wherein step a is carried out in vivo.

* * * * *